United States Patent [19]

Picchietti et al.

[11] Patent Number: 5,427,577
[45] Date of Patent: Jun. 27, 1995

[54] SELECTIVELY PNEUMATIC BOWLING GLOVE

[75] Inventors: Remo N. Picchietti, Bannockburn; Remo N. Picchietti, Jr., Deerfield; Joseph Piagentini, Lake Villa; Mike Sledz, Vernon Hills, all of Ill.

[73] Assignee: DBA Products Co. Inc., Lake Bluff, Ill.

[21] Appl. No.: 200,943

[22] Filed: Feb. 23, 1994

Related U.S. Application Data

[63] Continuation of Ser. No. 903,571, Jun. 24, 1992, abandoned, which is a continuation-in-part of Ser. No. 823,838, Jan. 17, 1992, abandoned.

[51] Int. Cl.$^6$ ............................................. A63B 69/00
[52] U.S. Cl. ........................................ 473/59; 473/62; 602/21; 2/161.1
[58] Field of Search ........................ 473/59, 61, 62, 63; 482/44, 45, 46, 47, 49, 50; 602/5, 13, 21; 2/16, 20, 159, 160, 161.1, 162, 163, 170

[56] References Cited

U.S. PATENT DOCUMENTS

| | | |
|---|---|---|
| Re. 28,480 | 7/1975 | Petrusek . |
| D. 299,261 | 1/1989 | Gruenspecht et al. . |
| D. 299,262 | 1/1989 | Gruenspecht et al. . |
| 2,924,458 | 2/1960 | Barry . |
| 2,943,859 | 7/1960 | Koski et al. . |
| 3,217,333 | 11/1965 | Sweet et al. . |
| 3,421,160 | 8/1967 | Domenico .................. 2/159 |
| 3,486,171 | 12/1968 | Zierhut ..................... 2/159 |
| 3,564,613 | 10/1969 | Frowler ..................... 2/159 |
| 3,728,738 | 4/1973 | Andolino . |
| 3,755,820 | 9/1973 | Petrusek . |
| 3,992,723 | 11/1976 | Lazanas . |
| 4,067,063 | 1/1978 | Ettinger . |
| 4,095,294 | 6/1978 | Winterbottom . |
| 4,121,312 | 10/1978 | Penney . |
| 4,138,108 | 2/1979 | Robinson ................. 273/54 B |
| 4,168,063 | 9/1979 | Rowland ................. 273/54 B |
| 4,222,569 | 9/1980 | DeMascolo ............... 273/183 |

(List continued on next page.)

FOREIGN PATENT DOCUMENTS

| | | |
|---|---|---|
| 0389215 | 9/1990 | European Pat. Off. . |
| DE3326085 | 4/1985 | Germany . |
| WO90/04323 | 5/1990 | WIPO . |
| WO90/09115 | 8/1990 | WIPO . |
| 9112054 | 8/1991 | WIPO . |

OTHER PUBLICATIONS

EBONITE ® "Gloves & Accessories," 1989, p. 1–5.
SARANAC "Super Striker" (package label and insert).
Robby's TM "Presents . . . a Glove for Every Bowler, Every Style and Every Technique!" flyer.
Robby's TM "Professional Bowling Products" flyer.
Schouwen, Daryl Var, "Spaulding Pumps Up New Glove," Chicago Sun–Times, Jul. 16, 1991.
Pereira, Joseph, "From Air to Pump to Puma's Disc System, Sneaker Gimmicks Bound to New Heights," Wall Street Journal, Oct. 31, 1991.

*Primary Examiner*—Vincent Millin
*Assistant Examiner*—W. Pierce
*Attorney, Agent, or Firm*—Leydig, Voit & Mayer, Ltd.

[57] ABSTRACT

An athletic support device in the nature of a brace for use in bowling, having a casing that extends along a portion of the hand and/or wrist, means for coupling the casing to the hand, at least one inflatable bladder associated with the casing located at the position or positions where support is desired, and means for providing gas to the inflatable bladder so that the bladder may be inflated to provide support to the hand and/or wrist, as desired. The device includes means for deflating the bladder or bladders, so that the level of support provided may be adjusted to a desired level. The bladders may be incorporated into conventional support device designs, such as gloves, braces, and wraps. Preferably, bladders are associated with the casing at one or more of the following areas: palm area, wrist area, or finger area. In this way, the device may be tailored to the bowler's hand or to provide an optimal position of the hand and/or wrist for a desired delivery of the ball.

40 Claims, 10 Drawing Sheets

U.S. PATENT DOCUMENTS

| | | | |
|---|---|---|---|
| 4,281,647 | 8/1981 | Antypass . | |
| 4,547,919 | 10/1985 | Wang | 5/455 |
| 4,608,720 | 9/1986 | Purin . | |
| 4,619,250 | 10/1986 | Hasegawa . | |
| 4,628,911 | 12/1986 | Bornstein . | |
| 4,706,658 | 11/1987 | Cronin . | |
| 4,807,606 | 2/1989 | Hasegawa et al. . | |
| 4,817,304 | 4/1989 | Parker et al. . | |
| 4,899,763 | 2/1990 | Sebastian et al. | 128/878 |
| 4,903,864 | 2/1990 | Shirhan . | |
| 4,912,861 | 4/1990 | Huang . | |
| 4,945,571 | 8/1990 | Calvert . | |
| 4,965,886 | 10/1990 | Ockels . | |
| 4,974,343 | 12/1990 | Davidson . | |
| 4,974,344 | 12/1990 | Ching . | |
| 4,995,173 | 2/1991 | Spier . | |
| 4,999,932 | 3/1991 | Grim . | |
| 5,014,366 | 5/1991 | Discipio, Sr. | 2/424 |
| 5,014,689 | 5/1991 | Meunchen et al. | 2/161 A X |
| 5,020,515 | 6/1991 | Mann et al. . | |
| 5,025,502 | 6/1991 | Raymond et al. . | |
| 5,042,176 | 8/1991 | Rudy . | |
| 5,056,504 | 10/1991 | Mann | 128/DIG. 20 X |
| 5,113,530 | 5/1992 | Smith | 2/19 |
| 5,155,864 | 10/1992 | Walker et al. | 2/18 |
| 5,218,719 | 6/1993 | Johnson | 2/19 |
| 5,309,573 | 5/1994 | Solar et al. | 2/162 |

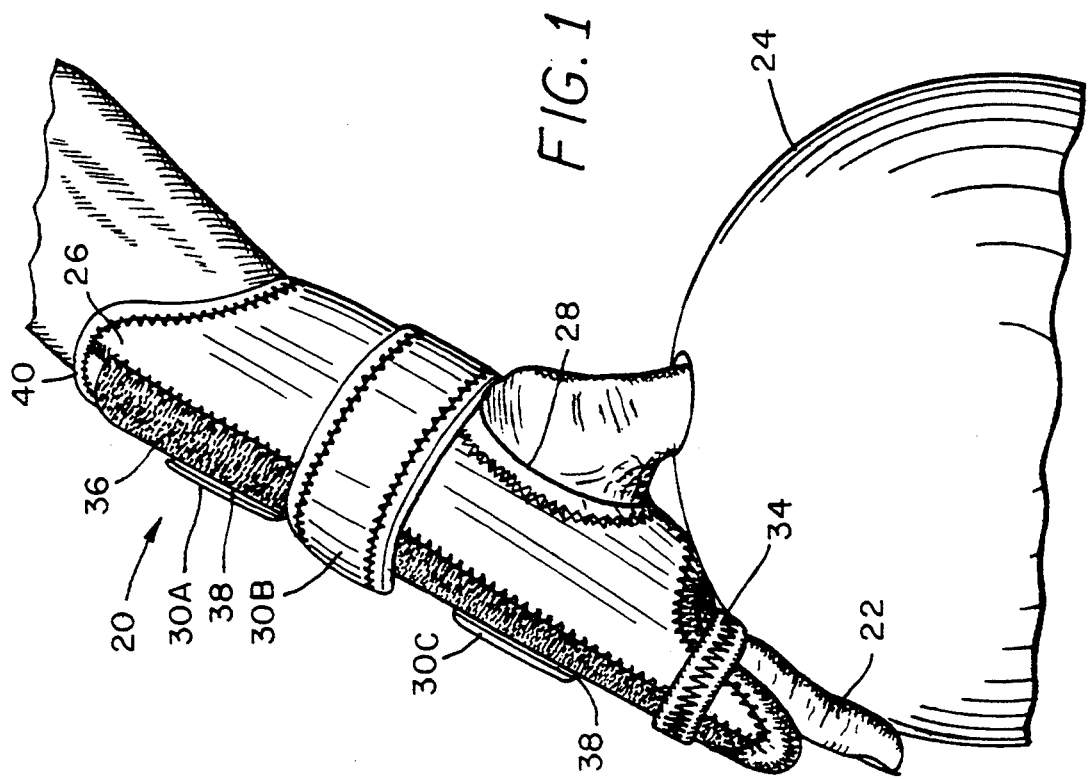
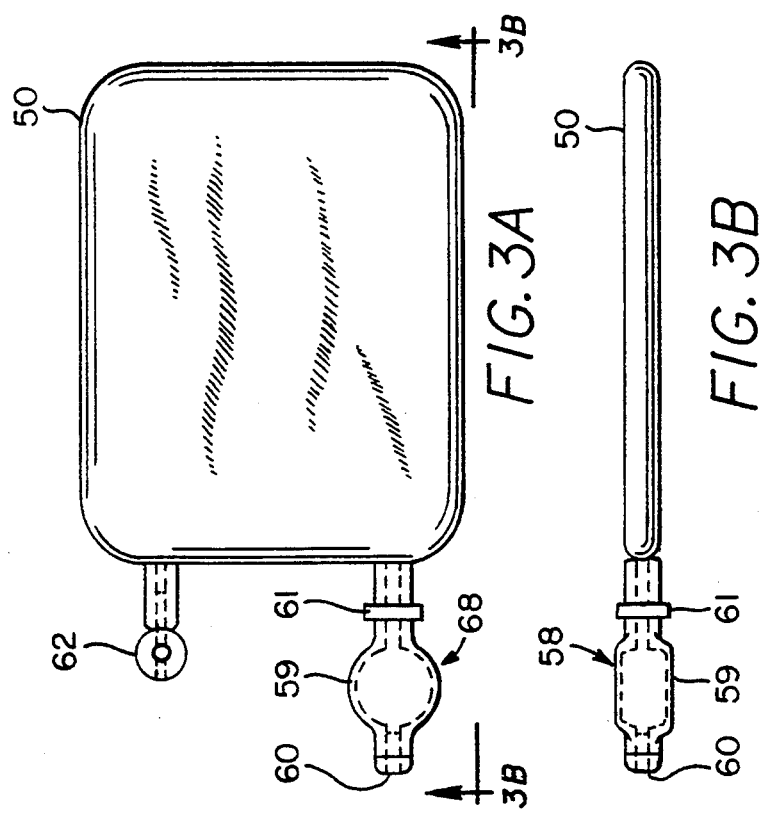

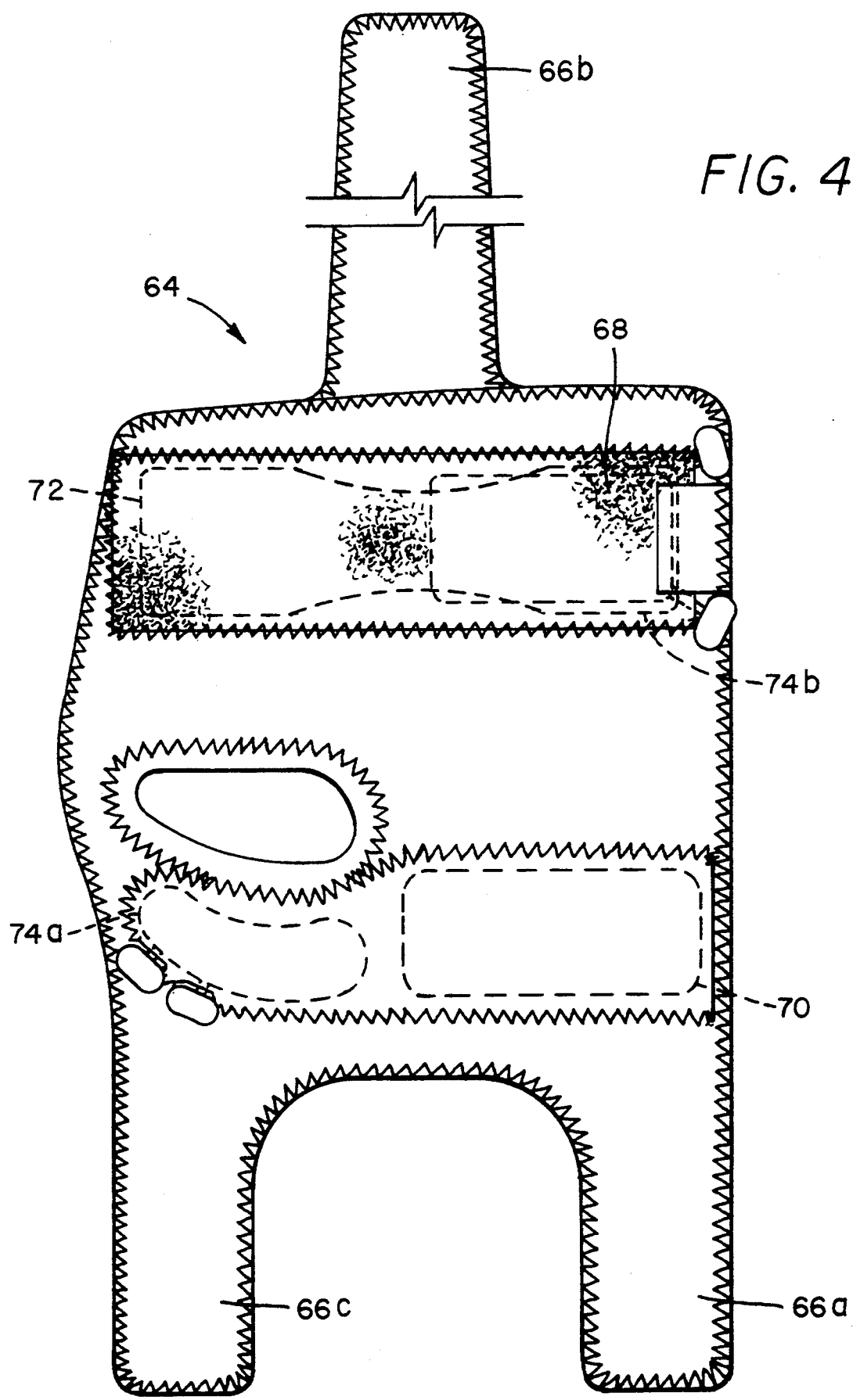

SELECTIVELY PNEUMATIC BOWLING GLOVE

This is a continuation of application Ser. No. 07/903,571 filed on Jun. 24, 1992, which is now abandoned, which is a continuation-in-part of application Ser. No. 07/823,838 filed Jan. 17, 1992, now abandoned.

FIELD OF THE INVENTION

The invention relates generally to bowling aids, and more specifically to athletic support devices for supporting a human hand while bowling.

BACKGROUND OF THE INVENTION

Athletic support devices are frequently used by bowlers for added comfort or control of the ball. Such devices may control the delivery of the ball by controlling, for example, the manner in which the ball is cradled in the bowler's hand, or the manner in which the ball is released. Further, these devices may provide support to the hand and/or wrist to control the movement of the hand, wrist, and forearm to prevent movements such as "breaking."

A number of styles of support devices exist, which provide various desirable features, including gloves, splints, and wraps, which may likewise incorporate rigid splints. Gloves, for example, may include "tacky fingers" that have a higher coefficient of friction and provide the bowler with added control of the ball at release. Gloves may also provide added comfort to the bowler.

Splint-type devices and wraps that include rigid splints are generally used to limit the movement of the hand, wrist, and forearm. Splints are generally strapped to the hand and wrist, while wraps are generally wrapped around the wrist and/or hand and secured by straps, adherent materials such as Velcro TM, or the like. Splints and wraps may extend along the wrist and beside a portion of or the complete length of the hand.

While assisting the bowler by providing added support and limiting relative movement, these devices also have a number of disadvantages. For example, splints and wraps generally require various adjustments to ensure a proper fit to the bowler's hand and wrist. Moreover, as they are generally firmly strapped to the wrist and hand to partially immobilize the hand and to minimize relative movement between the wrist and forearm, splints and wraps can be quite uncomfortable. Thus, such devices can be particularly cumbersome and uncomfortable when the bowler is resting, as between frames. Further, because the device may be cumbersome and difficult to properly place on the hand, the bowler may be hesitant to remove or even loosen the device when resting. While gloves may be more comfortable, they do not provide the support or level of immobilization of splints or wraps.

Additionally, while such bowling aids are available in various sizes, they generally do not provide an optimal fit and are not easily adjusted to different bowlers. Likewise, such devices are not readily adjustable to provide a different feel or form for consecutive ball deliveries.

OBJECTS OF THE INVENTION

It is a primary object of the invention to provide an athletic support device that may be easily adjusted to provide a desired level of support to the hand and/or wrist while bowling. It is a related object to provide a device that may be easily adjusted to provide optimal positioning of the hand for a desired delivery of the ball.

It is a further object of the invention to provide an athletic support device that may be easily adjusted to accommodate different hand sizes.

It is an additional object of the invention to provide an athletic support device that may be selectively adjusted to provide selected support to the particular areas of the hand and/or wrist desired.

Yet another object of the invention is to provide a comfortable athletic supporting device. A related object is to provide an athletic support device that may be easily adjusted to reduce the support pressure exerted on the hand and/or wrist between bowls.

BRIEF SUMMARY OF THE INVENTION

In accomplishing these objectives, the invention provides an athletic support device in the nature of a brace having a casing that extends along a portion of the hand and/or wrist, and means for coupling the casing to the hand. At least one inflatable bladder is associated with the casing and is located at the position or positions where support is desired. The support device further comprises means for providing gas to the inflatable bladder(s). In this way the bladder(s) may be selectively and controllably inflated by the user during use to provide a desired level of support to the hand and/or wrist.

The currently preferred locations of the bladders are in the palm area of the device, and in the finger and wrist areas along the back side of the hand. One or more bladders may be selectively inflated to a desired level to provide support to the hand and/or wrist. In this way, the device may be tailored to the bowler's hand or to provide the optimal position of the hand and/or wrist for a desired delivery of the ball. For example, the wrist support may be inflated to provide the optimal hand and wrist position for delivery of a ball that hooks to the left, or the finger support may be inflated to provide the optimal position for delivery of a ball that hooks to the right.

While the device may be incorporated into a number of generally conventional support device designs, the invention provides added comfort over traditional support devices inasmuch as the device may be tailored to the particular bowler's hand. Additionally, the gas may be readily released from the bladders between shots, relieving the pressure against the hand as well as for readjustment as desired by the user for the next bowl.

These and other features and advantages of the invention will be more readily apparent upon reading the following description of a preferred exemplified embodiment of the invention and upon reference to the accompanying drawings wherein:

BRIEF DESCRIPTION OF THE DRAWINGS

FIG. 1 is a perspective view of an athletic hand-supporting device for bowling incorporating teachings of the present invention.

FIG. 3A is a front plan view of one of the bladders included in the glove of FIG. 1.

FIG. 3B is a side plan view of the bladder taken along line 3B—3B in FIG. 3A.

FIG. 4 is a plan view of another embodiment of an athletic hand-supporting device incorporating teachings of the present invention.

Figure 2:
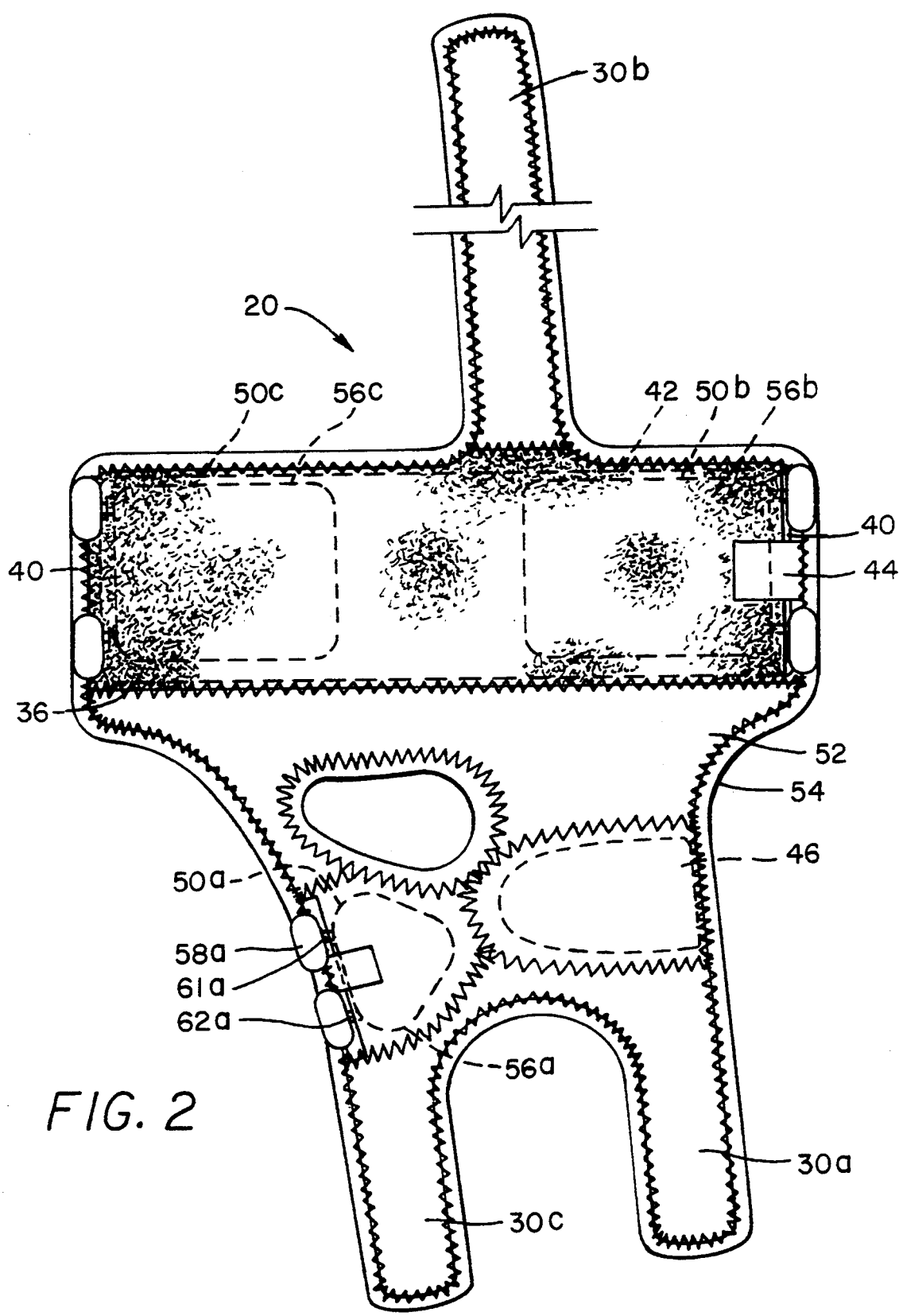
FIG. 2 is a plan view of the outside of the device of FIG. 1 removed from the hand.

While the invention will be described in connection with certain preferred embodiments, there is no intent to limit it to those embodiments. On the contrary, the intent is to cover all alternatives, modifications, and equivalents included within the spirit and scope of the invention as defined by the appended claims.

DETAILED DESCRIPTION OF THE ILLUSTRATED EMBODIMENTS

Turning now to the figures, there is shown in FIG. 1 one style of athletic supporting device 20 for supporting a human hand 22 during delivery of a bowling ball 24. The device 20 comprises a casing 26 having an opening 28 through which the thumb may be inserted. The casing 26 may be of a single layer, or multiple layers that extend the partial or complete length of the hand and/or wrist. In the embodiment exemplified in FIG. 1, the casing 26 extends substantially the entire length of the hand 22 and wrist and onto the respective adjacent portion of the forearm. Multiple layers may be provided to meet a variety of purposes. For example, a substantially rigid layer may be included to provide form to the device 20, a soft cushioning layer may be included to provide comfort, and/or an absorbent inner layer may be provided adjacent the hand to absorb perspiration, all in the manners known heretofore in such devices.

The casing 26 may be coupled to the hand by any appropriate means. In the device 20 shown, the user's thumb extends through an opening 28 in the casing 26 and the casing 26 is provided with straps 30a, b, c, which wrap around the hand and wrist of the bowler and a finger strap 34 that wraps around the fingers of the bowler. In the illustrated device 20, the finger strap 34 is detachable. The straps 30a, b, c, and 34 are wrapped tightly around the hand, wrist, and adjacent forearm of the bowler and then secured to the glove by securement means such as Velcro ™ adherent strips 36, 38, or the like provided along the outer surface of the device 20 along that portion of the casing 26 extending along the back of the hand, and the ends of the straps 30a, b, c, and 34, respectively.

The device 20 may be understood more readily with reference to FIG. 2, which shows a plan view of the outer surface of the device 20 removed from the hand of the bowler. In this view, the removable finger strap 34 is not illustrated. In order to provide additional support to the wrist of the bowler, a substantially rigid splint 40 is provided along the portion of the device 20 extending along the back of the hand. The splint 40 may be sewn into or formed with the casing 26, or, alternately, removably inserted into a pocket 42 extending longitudinally along the back portion of the device, as shown in FIG. 2. The splint 40 may be held in place in the pocket 42 by a Velcro ™ adherent flap 44, or the like. It will be appreciated that the splint 40 may extend the length of the device 20 or, alternately, only a portion of the distance along the back portion of the device 20. The splint 40 may be fabricated from any appropriate material. For example, steel and rigid plastic materials are particularly suitable. Further, the splint 40 may be of any appropriate shape. In the embodiment shown, the splint 40 is of a substantially flat rectangular shape. However, the splint could alternately be of an "hour glass" shape or the like in plan view and/or arcuate or angular in side view to provide added comfort to the bowler or facilitate improved fit and hand positioning.

In order to provide increased support to the hand or wrist of the bowler, the device 20 may be provided with a palm splint 46 either alone or in conjunction with the back splint 40. The palm splint 46 may be disposed in a pocket 48 along the palm side of the support device 20 to provide support to the palm and/or wrist, as desired. As with the back splint 40, the palm splint 46 may be integrally formed with the casing 26, or removably inserted into or sewn integrally with the casing 26, and may be of any appropriate design to provide a desired type of support. In the embodiment shown, the palm splint 46 is not readily removable, as it is sewn integrally with the casing 26. Further, the palm splint 46 extends only a portion of the way across the palm portion of the device 20 so as to provide added support to the wrist only. The palm splint 46, however, could likewise be designed to extend further into the palm area to provide additional support to the palm of the hand or assistance in positioning the ball.

In accordance with the invention, the support device 20 is provided with one or more inflatable bladders 50a, b, c associated with the casing 26 to provide selective support to a bowler's hand and/or wrist. The invention further comprises means for selectively and controllably providing gas to each of the bladders 50a, b, c to inflate the bladders to provide support for the hand. The support device 20 may additionally be provided with means for releasing gas from the inflatable bladders 50a, b, c. Thus, the invention contemplates a reusable support device wherein the bladders may be selectively inflated and deflated to provide the degree and placement of support desired by the bowler, as well as a support device that may be customized for the bowler's hand and wrist.

The bladders 50a, b, c may be formed of any appropriate gas impervious material, such as latex or urethane, and any appropriate shape, such as rectangular or oval. Further, the bladders 50a, b, c may be of any appropriate surface construction. For example, each bladder 50a, b, c may have a smooth outer surface, a quilted outer surface or a reinforced outer surface and/or localized attachment of opposite walls to one another within the bladder outline to provide additional control of the expansion of various portions of the respective bladder.

The bladders 50a, b, c may be directly associated with the surface of the casing 26. Alternately, where the casing 26 includes multiple layers of material, the bladders 50a, b, c may be disposed between the layers. When the bladders 50a, b, c are disposed between layers of the casing 26, a pocket may be formed between the layers, the bladder 50 being disposed within the pocket. Alternately, if the layers are formed of materials that are gas impervious, adjacent layers of the casing 26 may be sealed together to form a bladder therebetween.

In the embodiments illustrated, each bladder 50a, b, c is provided with an independent inflating means 58 for providing gas to the respective bladder 50, as well as a release valve 62 for releasing gas from the respective bladder 50, whereby each bladder may be controllably inflated and deflated independently of the condition of the other bladder. This facilitates customized fitting and control of the positioning of the user's hand and/or wrist.

As shown in the exemplary embodiment illustrated in FIG. 3, the inflating means 58 may be of any appropriate design, such as a rubber, spherical thumb pump 59 with a back valve 60. In order to provide a one-way flow of gas from the thumb pump 59 into the bladder, the inflating means 58 may include a one-way valve 61, such as a duck bill valve. The release valve 62 may likewise be of any appropriate design, such as a simple bleed valve, preferably of a "push to release" type. While a single inflating means 58 and release valve 62 may be provided for all of the bladders 50, the preferred embodiment utilizes an inflating means 58 and a release valve 62 for each bladder as noted above.

Returning now to the embodiment shown in FIG. 2, the bladders 50a, b, c may be disposed in the support device 20 to provide added support to areas such as in the palm of the hand (bladder 50a), behind the wrist (bladder 50b), and behind the fingers (bladder 50c). Turning first to the bladder 50a disposed in the palm area of the device 20, inflation of the palm bladder 50a fills the space created between the ball and the central palm portion of the hand (between the thumb and fingers) to provide increased comfort. It will further be appreciated that inflation of the palm bladder 50a varies the position in which the ball is cradled in the hand of the bowler, and therefore the release.

The bladder 50a may be utilized whether or not an additional palm splint 46 is provided. The palm splint 46 may be of the design such as the shape shown in FIG. 2 or of an elongated shape that extends down into the area adjacent the bladder 50a. If the splint 46 extends down into the palm area adjacent the bladder 50a, the bladder 50a may be disposed either between the splint 46 and the hand to provide added comfort and control of the ball, or toward the outside of the casing 26, between the splint 46 and the ball to provide control of the ball.

While the bladder 50a may be of any appropriate design, in the embodiment illustrated in FIG. 2, the bladder 50a is of a triangular shape. Moreover, the bladder 50a is of a wedge configuration (to inflate to a wedge shape), increasing in thickness from the inner point to the base of the triangle adjacent the valves 61a, 62a.

Turning next to the bladder 50b disposed in the wrist area of the device 20, the bladder 50b will preferably be disposed along the back side of the hand, extending along at least a portion of the back side of the hand, the wrist joint, and the forearm. As with the palm bladder 50a, the bladder 50b may be utilized whether or not a splint 40 is provided along the back side of the hand. It will be appreciated, however, that if such a splint 40 is provided, the bladder 50b should be disposed between the splint 40 and the inside surface of the device so that its inflation will exert pressure on the wrist of the bowler. Thus, whether or not the device 20 includes a splint 40, inflation of the wrist bladder 50b will provide a desired level of support to the back of the wrist to minimize or control the movement of the hand relative to the forearm.

Finally, the bladder 50c disposed in the finger area of the device 20 (outward of the first knuckle) may likewise be utilized whether or not the splint 40 is provided along the back of the hand. As with the wrist bladder 50b, if a splint 40 is provided, the finger-supporting bladder 50c is preferably disposed along the inside of the device 20, positioned adjacent the hand of the bowler, i.e., between the splint 40 and the hand. The finger bladder 50c may be inflated to provide increased support to the fingers and to effect a desired delivery of the ball.

In the embodiment illustrated in FIG. 2, the bladders 50b, 50c are of a generally rectangular shape, extending lengthwise along that portion of the device designed to lie adjacent the back of the bowler's hand and adjacent forearm. The palm bladder 50a is of a triangular, wedge shape, as explained above. Further, the device 20 utilizes both a splint 40 along the back of the hand, as well as a palm splint 46, which extends a portion of the way down the palm of the hand of the bowler. It will be appreciated, however, that the device might alternately include only one or two of the bladders, as explained with reference to FIGS. 8–10C. Similarly, the device could utilize no splints or only one splint, as likewise explained with reference to FIGS. 8–10C. The inclusion of splints provides rigid support references and may provide a cantilever action, particularly with elongated splints, whereby use of a bladder in one area also affects support in other areas remote from that bladder.

Turning now to the embodiment shown in FIG. 4, there is shown a similar wrap style support device 64. The device 64 shown in FIG. 4 differs from the device 20 shown in FIG. 2 in that it does not extend the length of the fingers. The device 64 may be positioned on the hand and secured thereto by straps 66a, b, c and Velcro ™ adherent strips 68, as explained with reference to the first embodiment shown in FIGS. 1 and 2. Further, the device 64 includes a palm splint 70 and a splint 72, which extends along the back side of the hand. It will be noted that in this embodiment the splint 72 is of an hour glass shape. Inasmuch as the device 64 does not extend down into the finger area of the bowler, only a palm bladder 74a and a wrist bladder 74b are provided.

Figure 5A:
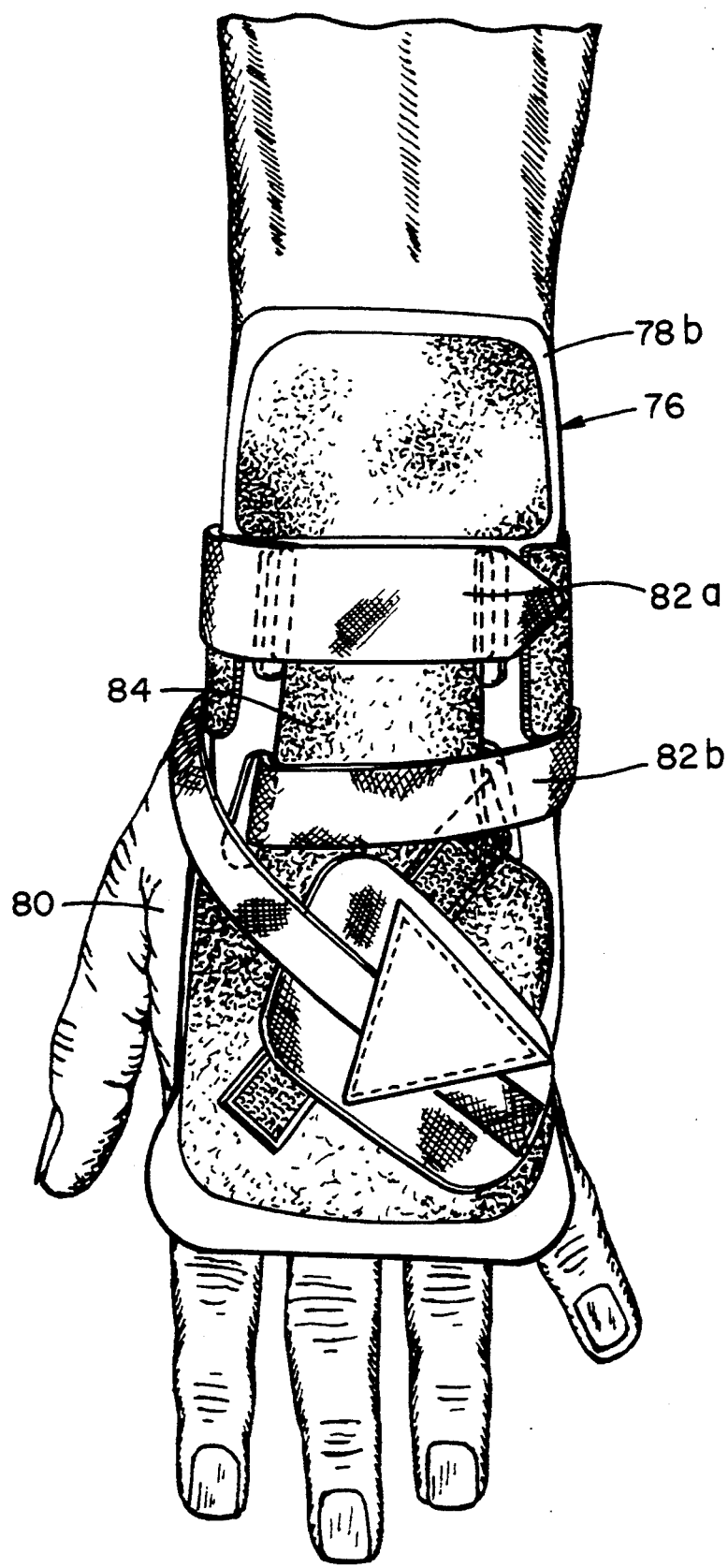
FIG. 5A is a perspective view of another embodiment of an athletic hand-supporting device incorporating teachings of the invention secured to a hand by straps.
Figure 5B:
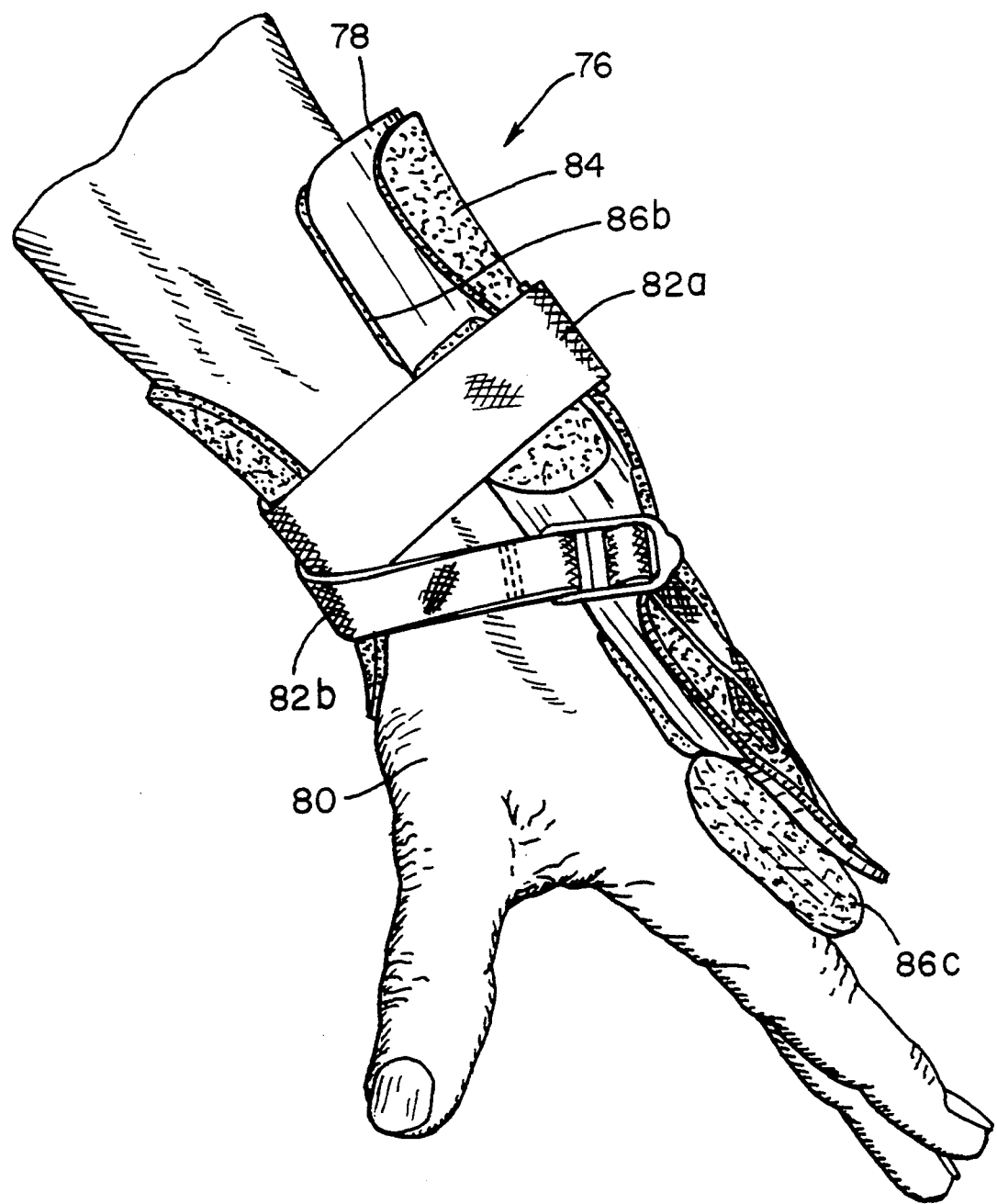
FIG. 5B is a side view of the supporting device in FIG. 5A.
Figure 5C:
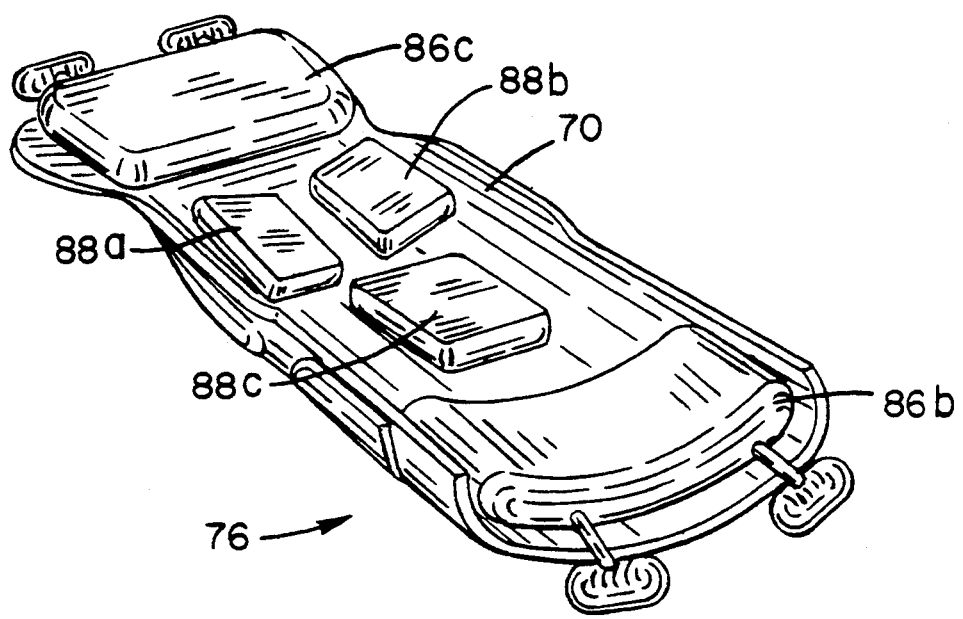
FIG. 5C is a perspective view of the underside of the supporting device of FIG. 5A.

A third embodiment of the invention is shown in FIGS. 5A, 5B, and 5C. This device 76 includes a rigid splint 78 that is secured to the back side of the hand by multiple straps 82a, b which wrap around the hand and are secured to the splint 78 by adherent strips of Velcro ™ 84 or the like. As may be seen in FIG. 5C, this embodiment includes a wrist support bladder 86b and a finger support bladder 86c, which may be selectively and controllably inflated to provide a desired level of support or a desired hand position 27 25 for release of the ball. While, as illustrated, the device 76 includes a number of pads 88a, b, c disposed along the back side of the hand, it will be appreciated that an additional bladder or bladders could likewise be provided in this area.

Figure 6A:
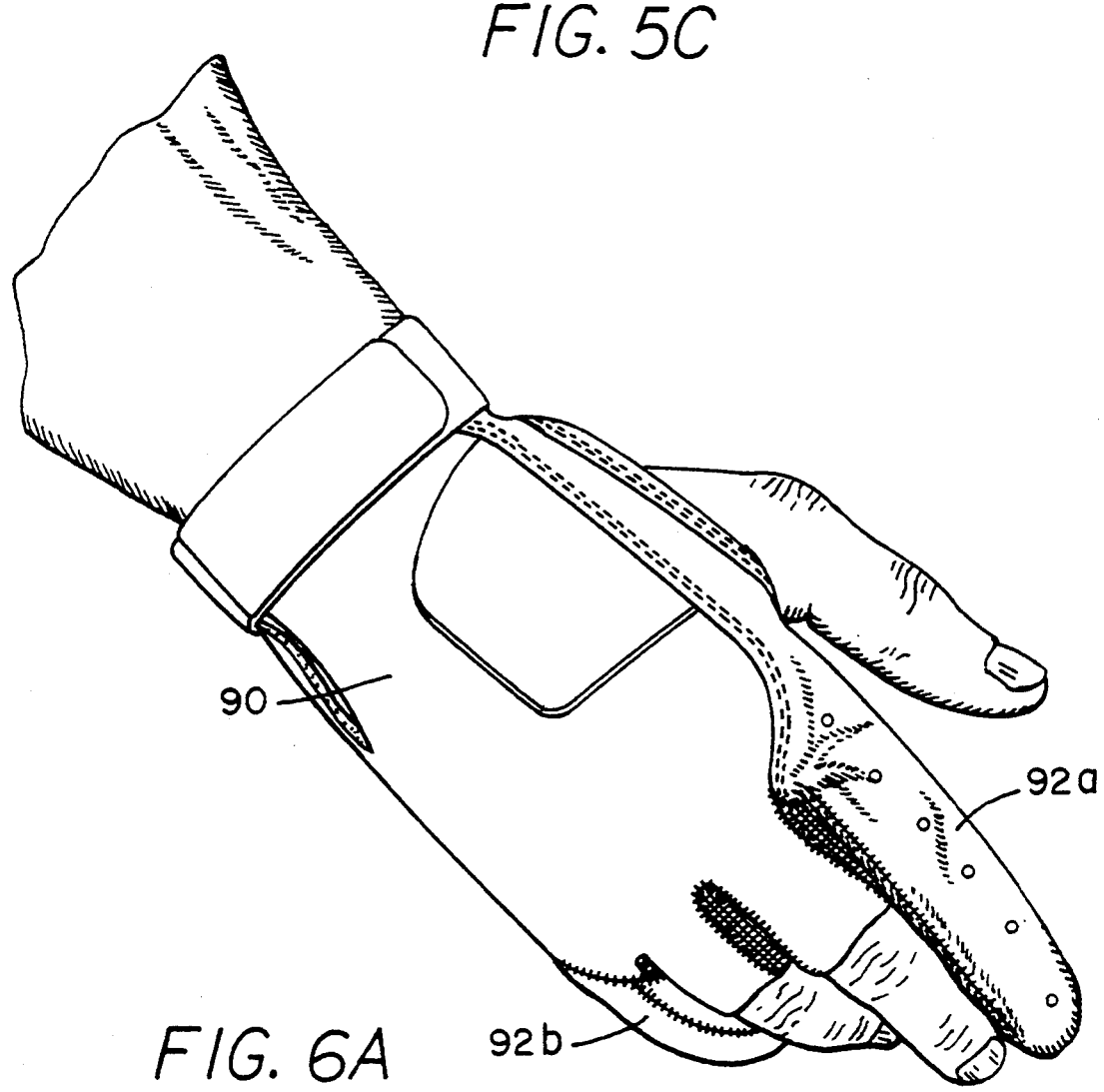
FIG. 6A is a perspective view of another embodiment of an athletic hand-supporting device incorporating teachings of the present invention secured to a hand.
Figure 6B:
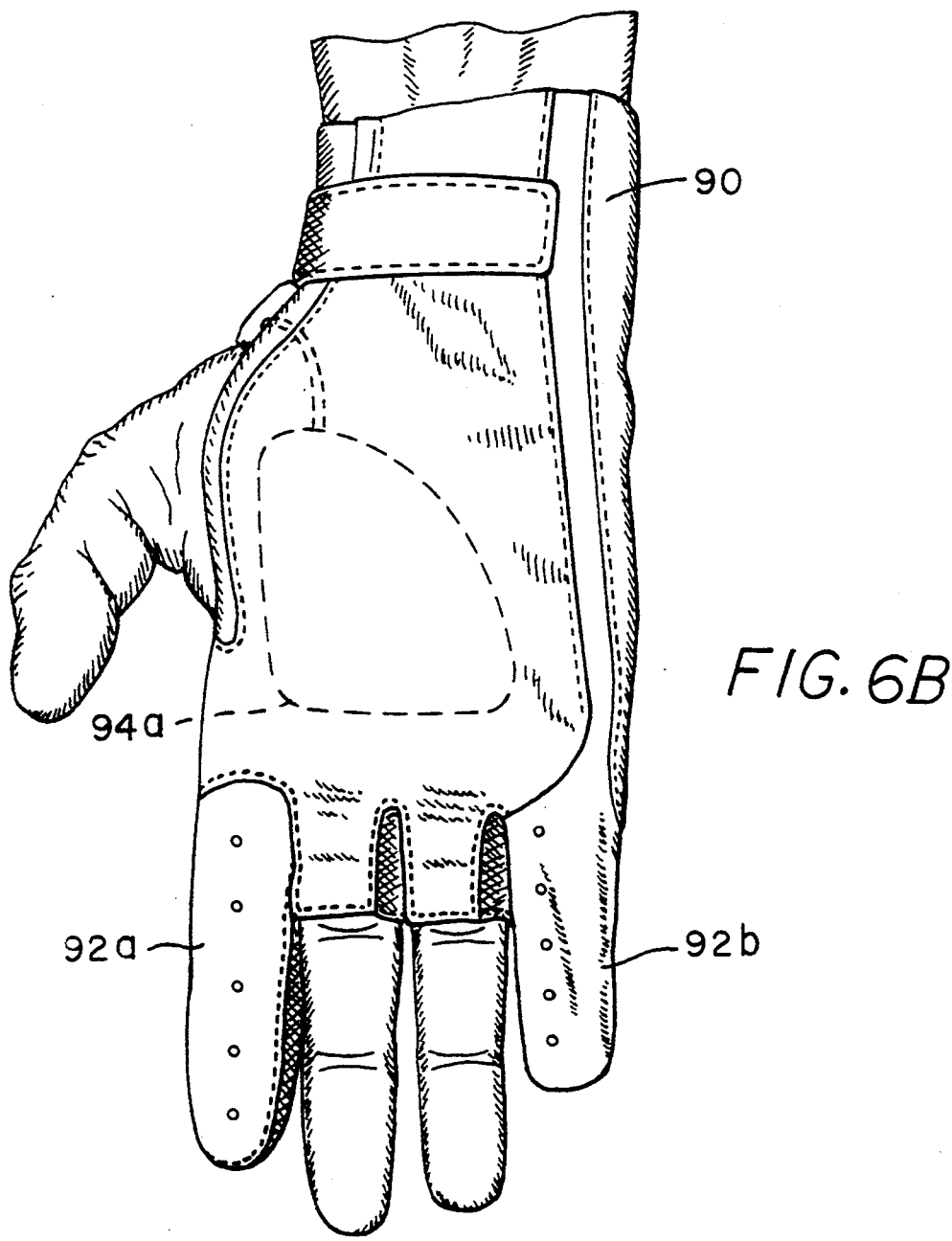
FIG. 6B is a plan view of the device of FIG. 6A from the palm side of the device.

A fourth embodiment of the invention is shown in FIGS. 6A and 6B. This embodiment includes a glove 90, such as the type which includes "tacky fingers" for the index and baby fingers 92a, b. The currently preferred embodiment for this type of glove 90 includes only a palm bladder 94a.

Figure 7A:
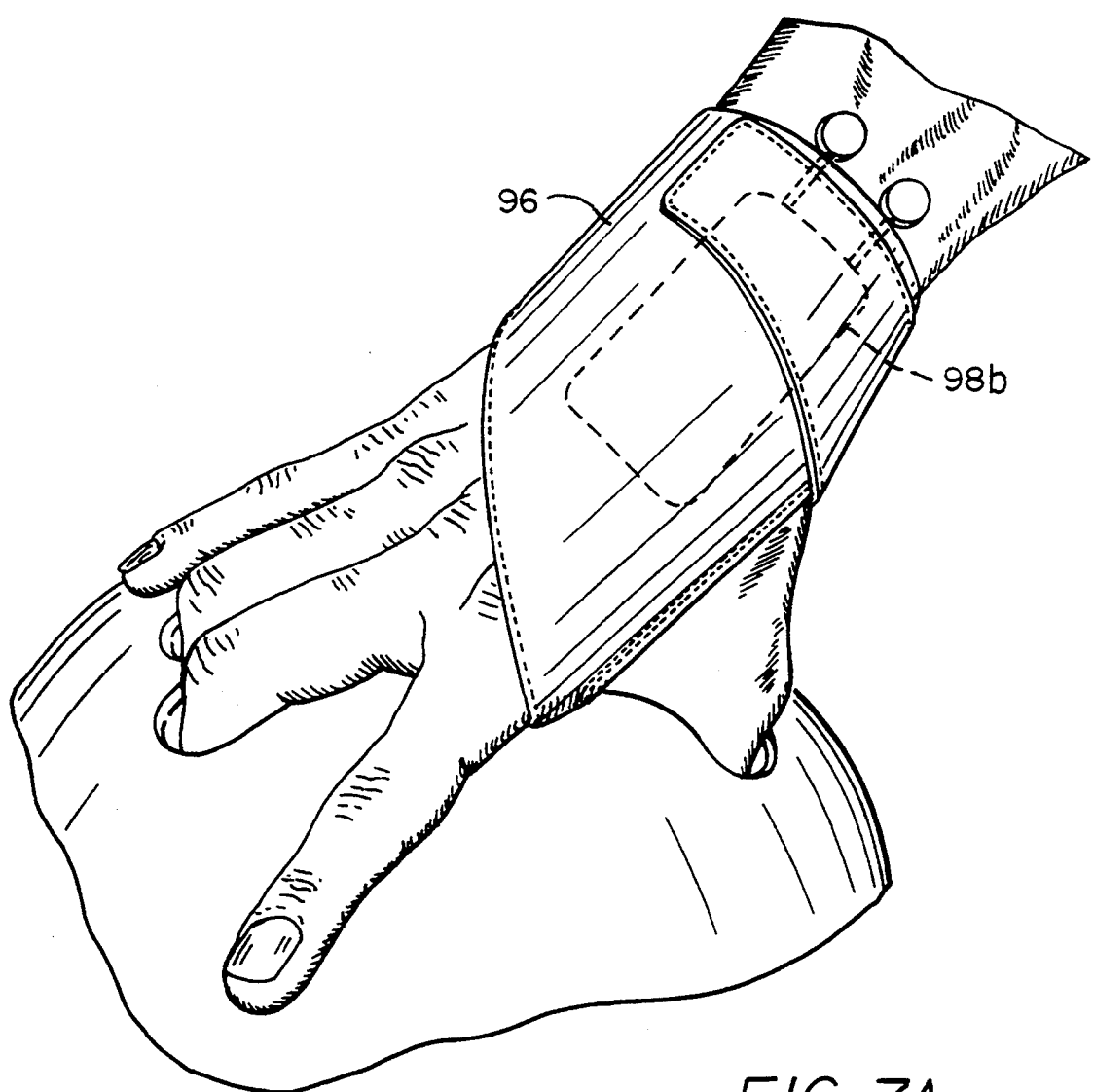
FIG. 7A is a perspective view of another embodiment of an athletic hand-supporting device incorporating teachings of the present invention secured to a hand.
Figure 7B:
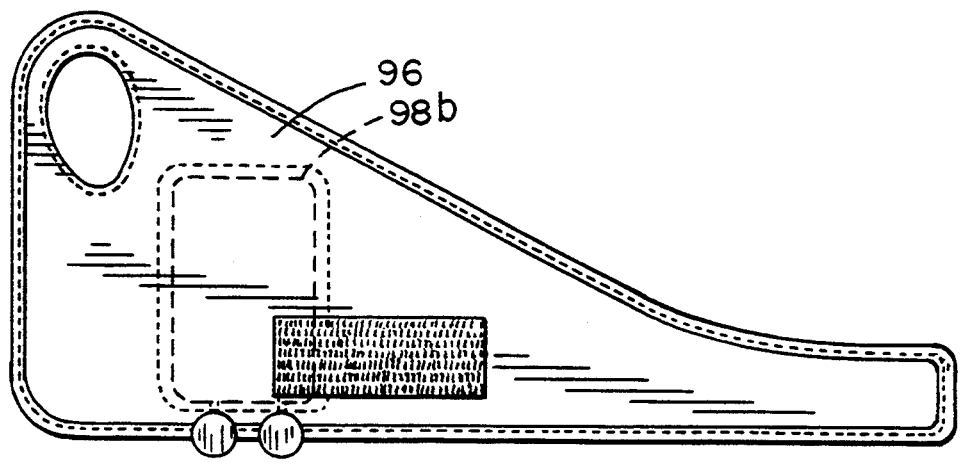
FIG. 7B is a front view of the outside of the device of FIG. 7A removed from the hand.

A fifth embodiment of the invention, as shown in FIGS. 7A and 7B, is a so-called "wrist wrap" 96, which wraps around the wrist and is secured by a Velcro TM adherent strip, or the like. The currently preferred embodiment of this design utilizes only a single bladder 98b of suitable configuration disposed along the back side of the hand and wrist. It will be appreciated, however, that in order to obtain additional support, the wrap 96 might be provided with an additional bladder disposed along the inside of the wrist.

Finally, the currently preferred embodiment of the invention is shown in FIGS. 8–11. This embodiment is similar to the device 20 shown in FIGS. 1–3B in that the device 120 includes a casing 126 which extends substantially the entire length of the hand and wrist and includes an opening 128 through which the thumb may be inserted. (For ease of explanation, the reference numbers for elements of the device 120 used in the description of this embodiment that are analogous to elements of the embodiment illustrated in FIGS. 1–3B will be designated by the numbers used in the description of the first embodiment plus one-hundred, i.e., 1XX. Further details of those elements or additional elements will be designated by numbers over 170.) The device 120 is provided with straps 130a, b, c, which wrap around the hand and wrist of the bowler to secure the device 120 to the bowler's hand and forearm. The device 120 may further include a finger strap (not shown). In this embodiment, rather than the entire portion of the device 120 which covers the back of the hand being covered with Velcro TM, two thin parallel Velcro TM strips 136a, b or the like extend lengthwise along the outer surface of the device 120 along the back of the hand. Velcro TM pads are likewise provided at the ends of the straps 130a, b, c, respectively. It will be appreciated, however, that alternate attachment means may be provided.

In this embodiment, the device 120 comprises only palm and wrist bladder assemblies 170a, b, which include bladders 150a, b. The wrist bladder 150b has a substantially rectangular shape, while the palm bladder 150a has a substantially truncated triangular shape. While a bladder 150 the shape of the wrist bladder assembly 150b is shown in greater detail in FIGS. 9A and 9B, it will be appreciated that the palm bladder 150a is of a similar construction. The bladders 150 preferably are fabricated from a gas impervious material, such as rubber. The preferred embodiment utilizes a polyurethane material.

While the bladders 150 may be formed in any appropriate manner from any appropriate material, they are preferably formed from two sheets of material which are sealed together around the edges by ultrasonic welding or some other appropriate method to form the bladder chamber therebetween. When sealed together around the edges, a flange 172 is formed which extends laterally beyond the gas-tight sealed bladder cavity all around its periphery. It will be appreciated that the flange 172 may be pierced without puncturing the bladder 150. Consequently, the bladder assembly 170 may be sewn into position in the device 120 without damaging or detracting from the operation of the bladder 150 itself.

The device 120 includes means for controlling expansion of the bladders 150a, b during use. In the preferred embodiment illustrated, localized attachments 174a, b are provided between the opposed walls of the bladders 150a, b to control the configuration of the bladder in its expanded states. The interface attachments 174a, b may be formed by any appropriate method. In the illustrated bladder 150b, the interface attachments are disposed in a generally uniform pattern, being substantially uniformly spaced from one another and from the peripheral bond. Accordingly, the bladder inflates to a quilted pattern of substantially uniform thickness between each adjacent pair of attachments, thereby provided an effectively uniform thickness through the entire central area of the bladder when inflated. It will be appreciated, however, that the bladder 150 and the localized attachments 174 may be formed such that the bladder inflates to an alternate shape, e.g., a wedge shape or the like, e.g. by the number, distribution and configuration of the areas of interface attachments.

Figure 9A:
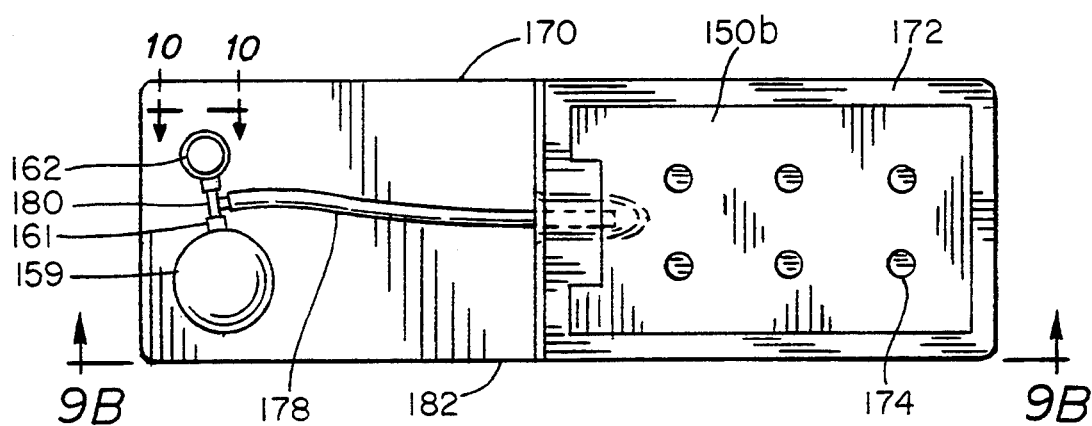
FIG. 9A is a front plan view of one of the bladders included in the glove of FIG. 8.
Figure 9B:
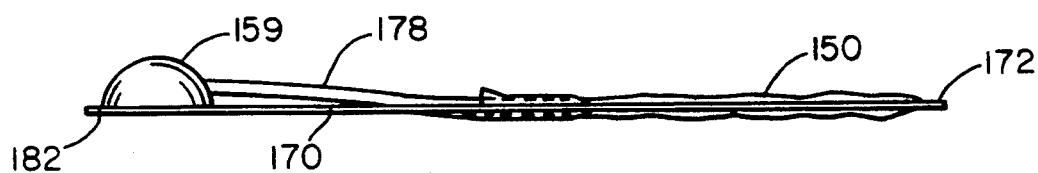
FIG. 9B is a side plan view of the bladder taken along line 9B—9B in FIG. 9A.
Figure 10:
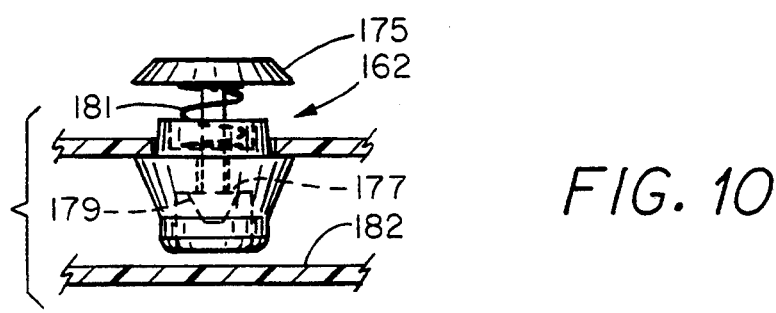
FIG. 10 is an enlarged side view of a release valve included in the glove of FIG. 8, taken along line 10—10 in FIG. 9A.

As shown more clearly in FIGS. 9A and 9B, a rubber spherical thumb pump 159 with a duck bill valve 161 and a release valve 162 control the flow of air or gas into and out of the bladder 150. The release valve 162, which is shown in more detail in FIG. 10, may be of a standard spring actuated release type.

As disclosed, the plunger 175 includes a surface 177 which is urged to a closed position against a valve seat 179 by a spring 181. The user presses the plunger 175 downward by finger pressure to effect release of air from the bladder. While the air flow controls 159, 161, and 162 may be coupled directly to the bladder 150, in the preferred embodiment of the invention the bladders 150 are disposed at one end of the device 120 and the air flow controls are disposed at the opposite end, being connected to the bladder 150 by a coupling tube 178. The pump 159 and release valve 162 are coupled to one end of the tube 178 by a T-connector 180 or the like, while the other end of the tube 178 is coupled to the bladder 150. The joints between the components are sealed to prevent any leakage, e.g. by being ultrasonically welded.

In order to assist in the positioning of the bladder assembly 170 within the device 120, the bladder assembly 170 further includes an assembly element 182, which forms a surface to which the coupling tube 178, the pump 159, and the release valve 162 are coupled, as shown in FIGS. 9A and 9B. The assembly element 182 may be an extension of the bladder material itself, or, alternately, it may be a separate piece of material to which the bladder 150 and the gas flow controls 178, 159, 162 are secured by any appropriate means. In the preferred embodiment, the element 182 is an extension of the bladder material itself and the gas flow controls 178, 159, and 162 are simply coupled thereto by glue or the like. The bladder assembly 170 is then sewn into place in the device 120.

Figure 11:
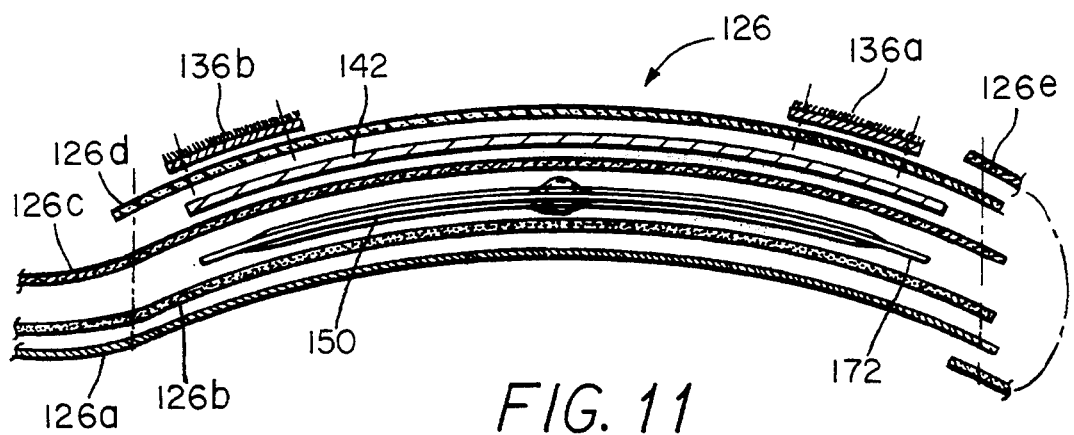
FIG. 11 is an exploded, fragmentary cross-sectional view of the supporting device taken generally along line 11—11 in FIG. 8.

The casing 126 may include multiple layers, as shown in greater detail in the exploded, fragmentary view shown in FIG. 11. It will be appreciated, however, that the casing 126 may include additional or fewer layers than those illustrated, or a single layer. Further, the layers may extend over the partial or complete area of the device 120.

The preferred embodiment illustrated in FIGS. 8–11 includes three distinct layers 126a, b, and c, which extend the entire area of the device 120. So that the device 120 will be comfortable for extended athletic wear, an absorbent, breathable, inner layer 126a is provided adjacent the hand. A fabric manufactured by Cerise, style number 1252 is particularly suited for this application in that it is absorbent and includes channels which facilitate movement of perspiration away from the surface of the device 120 adjacent the hand. Other fabrics, however, may be equally suitable for this purpose.

In order to provide added comfort to the bowler during use, the casing 126 is additionally provided with an intermediate, soft cushioning layer 126b, which lies adjacent the inner, absorbent layer 126a. While the cushioning layer 126b may be fabricated from any appropriate material, plastic and foam materials are particularly suited for this intermediate layer. In addition to providing cushioning, a foam layer provides additional absorption of perspiration during use. The layer is preferably formed from a foam material, which may be closed or open cell. While the cushioning layer 126b, or foam, may be of any appropriate thickness, it has been determined that an ⅛ inch layer of foam material is adequate to provide a comfortable fit.

Finally, in order to provide durability and form to the device 120, preferably a semi-rigid outer layer 126c is provided. Additionally, the outer layer 126c preferably provides a desirable appearance, even after extended wear. Consequently, the outer layer 126c is preferably resistant to soiling, and may be readily cleaned once soiled. Various artificial materials, such as plastics, and various natural materials, such as leather, cotton fabric, or the like, may be suitable. In the preferred embodiment, the outer layer 126c is formed from vinyl. Vinyl is a durable, semi-rigid material that is resistant to dirt or the like. Additionally, vinyl is relatively inexpensive and easy to work with, and may be readily wiped clean if it becomes soiled.

The bladder assemblies 170 are preferably disposed between the intermediate layer 126b and the outer layer 126c. For example, they may be sewn in place along the surface of the intermediate layer 126b before the outer layer 126c is assembled to the device 120.

To provide access to the pneumatic controls 159, 162, openings 190 are provided in the outer layer 126c. Further, in order to prevent damage to the controls 159, 162 and to provide a desirable appearance, control covers 192 are provided (see FIG. 8). The control covers 192 include resilient dome-shaped structures which cover the thumb pump 159 and the release valve 162. They may be fabricated from any appropriate material, but are preferably formed from a pliable, durable material, such as a rubber or other polymeric material. The control covers 192 may be sewn into place in the device 120 before the bladder assemblies 170 are assembled into the device 120.

Figure 8:
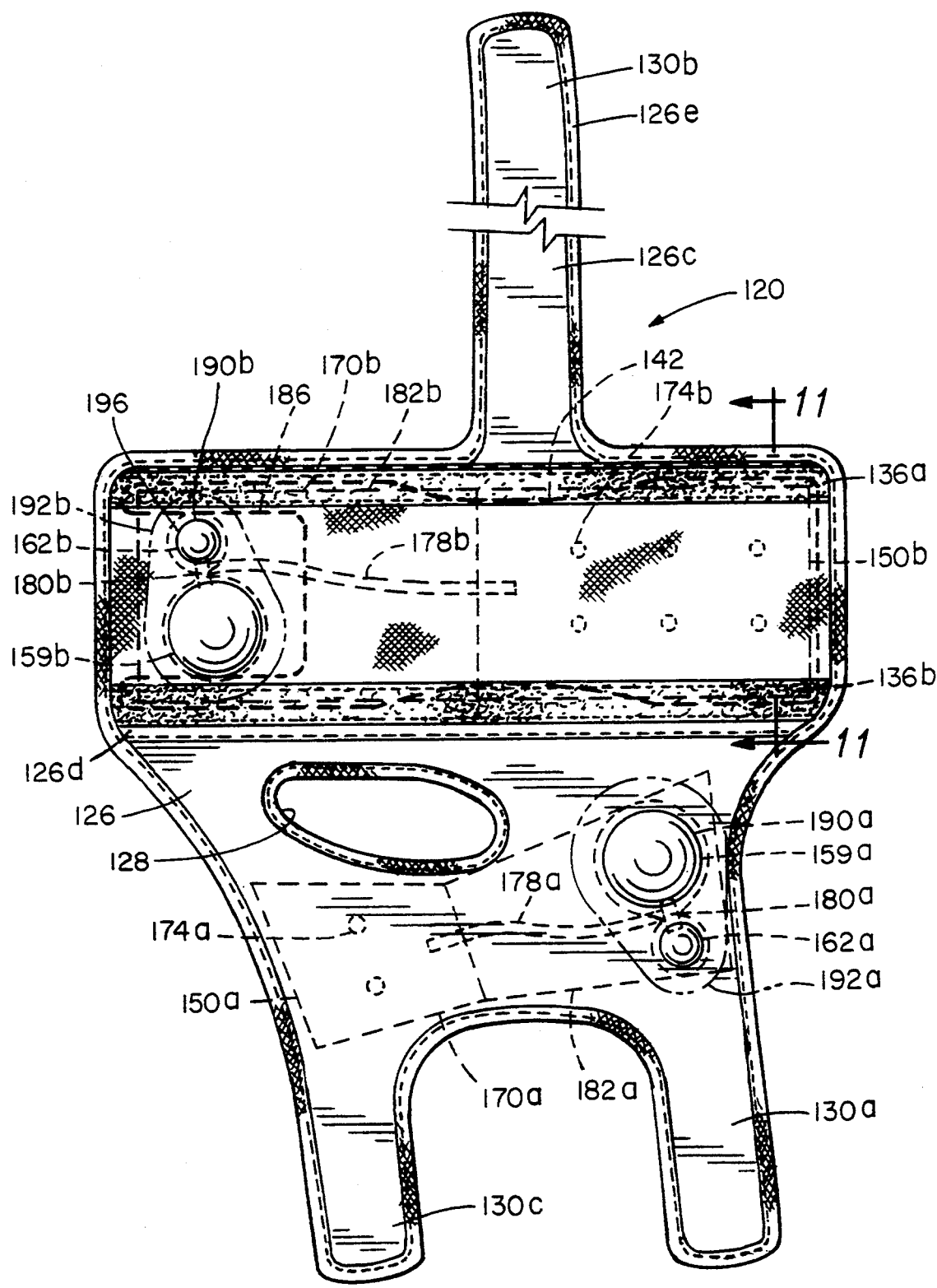
FIG. 8 is a plan view of the outside of another embodiment of an athletic hand-supporting device incorporating teachings of the present invention.

The preferred embodiment additionally includes a support brace 142. As shown in FIG. 8, in order to accommodate the pneumatic controls, the brace 142 includes a cutout 186.

In order to position the support brace 142 within the device 120, the embodiment illustrated includes an additional layer 126d, which is disposed along the outside of the back of the hand. As may be seen from the drawing, the additional layer 126d extends along only a portion of the outside surface of the device 120, and forms a pocket in which the support brace 142 is disposed. It will be appreciated that the layer 126d includes an opening 196 which corresponds to the opening 190b in the outer layer 126c for the controls 159, 162. The layer 126d may be secured to the outer layer 126c by any appropriate means, but the layers 126c, d are preferably stitched together. While the brace 142 may be removably disposed within the pocket between layers 126c and 126d, it is preferably sewn into the device 120 to reduce the possibility of damage to the pneumatic components of the device 120 due to the insertion and removal of the brace 126.

Finally, in order to ensure that layers 126a, b, c, d are adequately secured together and to prevent degradation of the layers 126a, b, c, d, due to raveling or the like of the fabrics, binding 126e is provided along the edges of the device 120. The binding 126e may be of any appropriate material. For example, the binding 126e may be of natural materials, such as leather or cotton, or synthetic materials, such as vinyl or polyester fabric. It will be appreciated that the binding additionally provides an attractive appearance to the device 120.

In summary, the invention provides a versatile athletic support device for bowling. One or more inflatable bladders and means for inflating the bladders may be associated with the casing of traditional devices to provide added control in delivering the ball and support for the hand and/or wrist of the bowler. The bladders may be selectively and controllably inflated in place by the user to tailor the support device to the hand of the bowler and to provide a desired hand position for each delivery of the ball. The support device further may be provided with one or more release valves, so that gas may be selectively released from the bladders, so that the device may be adjusted to change the position for an alternate type of delivery or to relieve pressure from the hand of the bowler, as between bowls.

The invention claimed is:

1. A bowling support device for selectively supporting a hand and/or wrist of a human while bowling, such hand having fingers, a palm and a back extending from a wrist which is joined to a forearm, the support device comprising:

a flexible hand-encompassing support casing having a surface area and configuration to extend around the hand of a bowler, said casing including a back portion and a front portion to extend across the back and palm of the hand of the user, respectively, and defining openings for projection of the thumb and mid-fingers of the bowler therethrough for gripping of a bowling ball, a plurality of non-intercommunicating inflatable bladders within the casing wherein each of said plurality of bladders is selectively inflatable independently of any inflation of the other said bladders, each of said bladders being of substantially lesser extent than said surface area of said casing and disposed in spaced relation from the other said bladders and at a position along the casing to engage only one of said back portion and said front portion in a desired location thereon which is spaced and distinct from the location of any other said bladders, to provide selectively adjustable support of the hand or wrist of the bowler in discrete locations where desired when bowling, and a plurality of independently operable inflating means within the support device, at least one of the inflating means being in pneumatic communication with each bladder, the inflating means selectively providing gas to the respective inflatable bladders during use so that the bladders inflate to thereby provide selectively adjustable support in the respective discrete areas.

2. The bowling support device as claimed in claim 1 further comprising at least one rigid splint within the casing disposed at a position along the casing where support is desired such that at least one of said bladders cooperates with said splint to provide selective pressure so as to selectively support at least one of the hand and wrist of the bowler when said device is in use.

3. The bowling support device as claimed in claim 1 wherein at least one of said bladders includes mutually opposed walls and means for controlling the separation of said opposed walls and thereby controlling the expanded shape of the bladder when the bladder is inflated.

4. The athletic support device as claimed in claim 3 wherein the means for controlling the relative positions of the walls comprises attachments between the opposed walls.

5. The athletic support device as claimed in claim 4 wherein the mutually opposed walls define an expansion zone of substantial lateral extent and are sealingly joined to one another around the perimeter of the expansion zone, the attachments being disposed within the expansion zone.

6. The athletic support device as claimed in claim 5 wherein the attachments are substantially uniformly distributed throughout the expansion zone.

7. The athletic support device as claimed in claim 5 wherein the attachments are substantially non-uniformly distributed throughout the expansion zone.

8. The bowling support device as claimed in claim 1 further comprising a plurality of release valves, one of said release valves and one of said inflating means being in pneumatic communication with each bladder.

9. The bowling support device as claimed in claim 8, wherein each of the inflating means comprises a pump.

10. The bowling support device as claimed in claim 9 further comprising at least one rigid splint within the casing disposed at a position along the casing where support is desired such that at least one of said bladders cooperates with said splint to provide selective pressure so as to selectively support at least one of the hand and wrist of the bowler when said device is in use.

11. The bowling support device as claimed in claim 1 wherein the casing includes palm and finger portions of configurations to extend along at least a portion of the palm and a portion of the fingers of the bowler, respectively, and the bowling support device comprises first and second such non-intercommunicating inflatable bladders, the first of said bladders being disposed along said palm portion of the casing and being inflatable to provide support to the palm of the bowler's hand, and the second of said bladders being disposed along said finger portion of the casing and being inflatable to provide such support to the fingers on the bowler's hand.

12. The bowling support device as claimed in claim 11 further comprising at least two release valves, wherein the inflating means comprises a pump, and one release valve and one pump are in pneumatic communication with each bladder such that each bladder can be inflated or deflated independently of the other of said bladders.

13. The bowling support device as claimed in claim 1 wherein the casing includes wrist and finger portions of configurations to extend along at least a portion of the wrist and forearm and a portion of the fingers of the bowler, respectively, and the bowling support device comprises first and second such non-intercommunicating inflatable bladders, the first of said bladders being disposed along said wrist portion of the casing and being inflatable to provide such support to the bowler's wrist, and the second of said bladders being disposed along said finger portion of the casing and being inflatable to provide such support to the bowler's fingers.

14. The bowling support device as claimed in claim 13 further comprising at least two release valves, and one release valve and one pump in pneumatic communication with each bladder such that each bladder can be inflated or deflated independently of the other of said bladders.

15. The bowling support device as claimed in claim 1 wherein the casing includes palm and wrist portions of configurations to extend along at least a portion of the palm and a portion of the wrist and forearm of the bowler, respectively, and the bowling support device comprises first and second such non-intercommunicating inflatable bladders, the first of said bladders being disposed along said palm portion of the casing and being inflatable to provide support to the palm of the bowler's hand, and the second of said bladders being disposed along said wrist portion of the casing and being inflatable to provide such support to the wrist.

16. The bowling support device as claimed in claim 15 further comprising at least two release valves, wherein the inflating means comprises a pump, and one release valve and one pump in pneumatic communication with each bladder such that each bladder can be inflated or deflated independently of the other of said bladders.

17. The bowling support device as claimed in claim 1 wherein the casing includes palm, finger and wrist portions of configurations to extend along at least a portion of the palm, a portion of the fingers, and a portion of the wrist and forearm of the bowler, respectively, and the bowling support device comprising first, second, and third such non-intercommunicating inflatable bladders, the first of said bladders being disposed along said palm portion of the casing and being inflatable to provide such support to the palm of the bowler's hand, the second of said bladders being disposed along said finger portion of the casing and being inflatable to provide such support to the bowler's fingers, and the third of said bladders being disposed along said wrist portion of the casing and being inflatable to provide such support to the bowler's wrist.

18. The bowling support device as claimed in claim 17 further comprising three release valves, wherein the inflating means comprises a pump, and one release valve and one pump in pneumatic communication with each bladder such that each bladder can be inflated or deflated independently of the other of said bladders.

19. The bowling support device as claimed in claim 1 wherein each of said first bladders includes mutually opposed walls and attachments between said walls for controlling the separation of said opposed walls and thereby controlling the expanded shape of the respective bladder when the respective bladder is inflated.

20. A bowling support device for selectively supporting a hand and/or wrist of a human while bowling, such hand having fingers, a palm and a back extending from a wrist which is joined to a forearm, the support device comprising:

a flexible support casing of a configuration to extend around such a hand of a bowler, said casing including a back portion to extend along at least the back of such hand of the bowler and along the back of at least one of the respective forearm and fingers of the bowler, means for coupling the casing to the hand, at least one rigid splint within the casing and disposed to extend along the back of said hand and along the back of said at least one of said forearm and said fingers, at least one inflatable bladder within the casing, said bladder being disposed at a position adjacent said rigid splint such that said bladder will be disposed intermediate at least a first portion of said splint and the back of at least one of said forearm, wrist, hand and fingers where support is desired when said device is in use, and at least one inflating means in pneumatic communication with said at least one inflatable bladder for selective manipulation by the user to provide gas to the inflatable bladder during use, so that the bladder inflates to provide selectively adjustable support between the splint and at least one of said forearm, fingers, hand and wrist and thereby to vary the relationship of the splint to another portion of said forearm, fingers, hand and wrist spaced along the splint from said first portion in a cantilever fashion while bowling.

21. The bowling support device as claimed in claim 20 wherein said rigid splint is disposed to extend along the back of said hand and along the back of said wrist and forearm, and a first inflatable bladder is disposed along a portion of said splint which is disposed such that said first bladder is intermediate a portion of said splint and the back of the wrist of the bowler when said device is in use, said first inflatable bladder being inflatable to provide such support to the wrist.

22. The bowling support device as claimed in claim 21 wherein the casing includes a palm portion of a configuration to extend along at least a portion of the palm of the bowler, a second inflatable bladder being disposed along said palm portion of the casing, the second inflatable bladder being selectively inflatable to provide selectively adjustable support to the palm of the bowler's hand.

23. The bowling support device as claimed in claim 21 wherein said first bladder includes mutually opposed walls, and attachments between said walls for controlling the separation of said opposed walls and thereby controlling the expanded shape of said bladder when the bladder is inflated.

24. The bowling support device as claimed in claim 20 wherein the casing includes a palm portion of a configuration to extend along at least a portion of the palm of the bowler, a second inflatable bladder being disposed along said palm portion of the casing, said second inflatable bladder being selectively inflatable to provide selectively adjustable support to the palm of the bowler's hand.

25. The bowling support device as claimed in claim 20 wherein the rigid splint is disposed to extend along the back of said hand and said fingers.

26. The bowling support device as claimed in claim 25 wherein a first inflatable bladder is disposed along a portion of said splint which is disposed such that said first bladder is intermediate a portion of the splint and the fingers of the bowler when said device is in use, the first inflatable bladder being selectively inflatable to provide selectively adjustable support to the fingers of the bowler's hand.

27. The bowling support device as claimed in claim 26 wherein said splint also is disposed to extend along at least a portion of the wrist and forearm, a second inflatable bladder being disposed along a portion of said splint which is disposed to extend substantially adjacent the wrist and forearm of the bowler when said device is in use, said second inflatable bladder being inflatable to provide such support to the bowler's wrist.

28. The bowling support device as claimed in claim 27 wherein the casing includes a palm portion of a configuration to extend along at least a portion of the palm of the bowler, a third inflatable bladder being disposed along said palm portion of the casing, the third inflatable bladder being selectively inflatable to provide selectively adjustable support to the palm of the bowler's hand.

29. The bowling support device as claimed in claim 26 wherein the casing includes a palm portion of a configuration to extend along at least a portion of the palm of the bowler, a second inflatable bladder being disposed along said palm portion of the casing, the second inflatable bladder being inflatable to provide support to the palm of the bowler's hand.

30. A bowling support device for selectively supporting a hand and/or wrist of a human while bowling, such hand having fingers, a palm and a back extending from a wrist which is joined to a forearm, the support device comprising:

a flexible hand-encompassing support casing having a surface area and configuration to extend around such a hand of a bowler, said casing including a back portion and a front portion to extend across the back and palm of such hand of the bowler, respectively, and defining openings for projection of the thumb and mid-fingers of the bowler therethrough for gripping of a bowling ball, said back portion of the casing including a wrist portion disposed to extend along at least a portion of the wrist of the bowler, an inflatable bladder within the casing, said bladder being of substantially lesser extent than said surface area of said casing and disposed along said wrist portion of the casing to engage only said back portion in a selected location thereon to be disposed adjacent the wrist of the bowler, an elongated rigid splint disposed along said back portion of the casing to be positioned along the back of the hand of the bowler and overlying said bladder disposed along the wrist portion of the casing, whereby said bladder will be disposed between said rigid splint and the wrist of the bowler when said device is in use, and at least one inflating means within the support device and in pneumatic communication with said at least one inflatable bladder for selective manipulation by the user to provide gas to the inflatable bladder during use, so that the bladder inflates to thereby provide selectively adjustable support for said wrist of the bowler.

31. The athletic support device as claimed in claim 30 wherein the casing includes an outer layer and an inner layer, the bladder being disposed between the layers, the inner layer adapted to be positioned adjacent the hand.

32. The athletic support device as claimed in claim 31 wherein the inner layer is fabricated from a substantially absorbent material.

33. The athletic support device as claimed in claim 31 wherein the outer layer is fabricated from a soil resistant material.

34. The athletic support device as claimed in claim 31 wherein the casing further comprises an intermediate layer.

35. The athletic support device as claimed in claim 34 wherein the intermediate layer is fabricated from a compressible material.

36. The bowling support device as claimed in claim 30 wherein the casing has a glove shape.

37. The bowling support device as claimed in claim 31 wherein the casing is wrapper shaped to extend around at least a portion of the palm and the back of the hand.

38. The bowling support device as claimed in claim 31 wherein the casing further extends around at least a portion of the wrist.

39. The bowling support device as claimed in claim 30 wherein the casing includes a plurality of layers and said bladder includes mutually opposed walls, said bladder being disposed between said layers, and attachments between said walls for controlling the separation of said opposed walls and thereby controlling the expanded shape of said bladder when the bladder is inflated.

40. A bowling support device for selectively supporting a hand and/or wrist of a human while bowling, such hand having fingers, a palm and a back extending from a wrist which is joined to a forearm, the support device comprising:

a flexible hand-encompassing support casing having a surface area and configuration to extend around such a hand of a bowler, said casing including a back portion and a front portion to extend across the back and palm of such hand of the bowler, respectively, and defining openings for projection of the thumb and mid-fingers of the bowler therethrough for gripping of a bowling ball, said back portion of the casing including a finger portion disposed to extend along at least a portion of the fingers of the bowler, an inflatable bladder within the casing, said bladder being of substantially lesser extent than said surface area of said casing and disposed along said finger portion of the casing to engage only said back portion in a selected location thereon to be disposed adjacent the fingers of the hand of the bowler, an elongated rigid splint disposed along said back portion of said casing to be positioned along the back of the hand of the bowler and overlying said bladder disposed along said finger portion of the casing, whereby said bladder will be disposed between said rigid splint and the fingers of the bowler when said device is in use, and at least one inflating means within the support device and in pneumatic communication with said at least one inflatable bladder for selective manipulation by the user to provide gas to the inflatable bladder during use, so that the bladder inflates to thereby provide selectively adjustable support for said fingers of the bowler.

* * * * *

UNITED STATES PATENT AND TRADEMARK OFFICE
CERTIFICATE OF CORRECTION

PATENT NO. : 5,427,577
DATED : JUNE 27, 1995
INVENTOR(S) : REMO N. PICCHIETTI, REMO N. PICCHIETTI, JR., JOSEPH PIAGENTINI AND MIKE SLEDZ

It is certified that error appears in the above-identified patent and that said Letters Patent is hereby corrected as shown below:

Column 15, claims 37 and 38, in each of lines 18 and 22, "claim 31" should read -- claim 30 --.

Signed and Sealed this

Twelfth Day of December, 1995

Attest:

*Attesting Officer*

BRUCE LEHMAN
*Commissioner of Patents and Trademarks*